United States Patent
Fulmer et al.

(10) Patent No.: US 10,036,380 B1
(45) Date of Patent: Jul. 31, 2018

(54) PERISTALTIC PUMP HEAD AND RELATED METHODS

(71) Applicant: Stenner Pump Company, Inc., Jacksonville, FL (US)

(72) Inventors: Fred Fulmer, Jacksonville, FL (US); Tim Ware, Ponte Verda Beach, FL (US); John Avery, St. Mary, GA (US); John Waycaster, Westminster, SC (US); Bill Harrington, Andover, CT (US)

(73) Assignee: STENNER PUMP COMPANY, INC., Jacksonville, FL (US)

( * ) Notice: Subject to any disclaimer, the term of this patent is extended or adjusted under 35 U.S.C. 154(b) by 0 days.

(21) Appl. No.: 15/685,090

(22) Filed: Aug. 24, 2017

Related U.S. Application Data (62) Division of application No. 14/548,481, filed on Nov. 20, 2014, now Pat. No. 9,759,210, which is a division of application No. 13/155,499, filed on Jun. 8, 2011.

(Continued)

(51) Int. Cl.
| | |
|---|---|
| F04B 43/12 | (2006.01) |
| A61M 5/142 | (2006.01) |
| B29C 65/70 | (2006.01) |
| F04B 53/22 | (2006.01) |
| F04B 43/08 | (2006.01) |
| B29C 65/02 | (2006.01) |

(Continued)

(52) U.S. Cl.
CPC ..... *F04B 43/1253* (2013.01); *A61M 5/14232* (2013.01); *B29C 65/02* (2013.01); *B29C 65/70* (2013.01); *F04B 43/08* (2013.01); *F04B 43/1276* (2013.01); *F04B 43/1284* (2013.01); *F04B 53/22* (2013.01); *B29K 2021/003* (2013.01); *B29L 2023/00* (2013.01); *F04B 43/12* (2013.01)

(58) Field of Classification Search
CPC .. F04B 43/12; F04B 43/1253; F04B 43/1276; F04B 43/1284; F04B 53/22; A61M 5/14232
See application file for complete search history.

(56) References Cited

U.S. PATENT DOCUMENTS

| | | |
|---|---|---|
| 2,696,173 A | 12/1954 | Jensen |
| 4,229,299 A | 10/1980 | Savitz et al. |

(Continued)

*Primary Examiner* — Peter J Bertheaud
(74) *Attorney, Agent, or Firm* — Allen Dyer Doppelt & Gilchrist (57) ABSTRACT

A peristaltic pump head includes a housing assembly adapted for mounting to a drive mechanism, a roller assembly arranged with the housing assembly and a flexible conduit extending through the housing assembly and engageable by the roller assembly to impel fluid therethrough. The roller assembly and the flexible conduit are removable from the housing assembly without disconnecting the entire housing assembly from the drive mechanism. The roller assembly can include an axially extending drive shaft, a roller control body fixedly mounted to the drive shaft, at least a first end plate rotatably mounted about the drive shaft, and at least a first roller arm pivotably mounted to the first end plate. The flexible conduit can include a length of hollow tubing made of an elastomeric material, and at least one overmolded end fitting made of a rigid polymeric material and fused to an end of the hollow tubing.

12 Claims, 7 Drawing Sheets

Related U.S. Application Data (60) Provisional application No. 61/352,560, filed on Jun. 8, 2010.

(51) Int. Cl.
  *B29K 21/00* (2006.01)
  *B29L 23/00* (2006.01)

(56) References Cited

U.S. PATENT DOCUMENTS

| | | | |
|---|---|---|---|
| 4,363,609 A * | 12/1982 | Cosentino | F04B 43/1276 417/477.5 |
| 4,496,295 A * | 1/1985 | King | F04B 43/1253 417/477.12 |
| 4,540,350 A | 9/1985 | Streicher | |
| 4,568,255 A | 2/1986 | Lavender et al. | |
| 4,631,008 A * | 12/1986 | Stenner | F04B 43/1253 417/477.1 |
| 4,650,471 A | 3/1987 | Tamari | |
| 4,976,590 A | 12/1990 | Baldwin | |
| 5,049,048 A | 9/1991 | Streicher | |
| 5,215,450 A | 6/1993 | Tamari | |
| 5,281,112 A | 1/1994 | Montoya et al. | |
| 5,895,695 A | 4/1999 | Rowley | |
| 6,135,158 A | 10/2000 | Kraus | |
| 6,171,082 B1 | 1/2001 | Hankner et al. | |
| 6,287,501 B1 | 9/2001 | Rowley | |
| 6,494,692 B1 | 12/2002 | Green | |
| 6,872,058 B2 | 3/2005 | Doig | |
| 7,001,561 B2 | 2/2006 | Nix et al. | |
| 7,252,485 B2 | 8/2007 | Ito | |
| 8,062,009 B2 | 11/2011 | Cueni | |
| 2002/0001530 A1 | 1/2002 | Doi et al. | |
| 2003/0138335 A1 | 7/2003 | Doi et al. | |
| 2005/0158196 A1 | 7/2005 | Schroeder et al. | |
| 2006/0151038 A1 | 7/2006 | Gregrich | |
| 2007/0051418 A1 | 3/2007 | Rowles et al. | |
| 2015/0252800 A1 | 9/2015 | Buckberry et al. | |

* cited by examiner

PERISTALTIC PUMP HEAD AND RELATED METHODS

CROSS-REFERENCE TO RELATED APPLICATIONS

This application is a divisional of U.S. patent application Ser. No. 14/548,481 filed on Nov. 20, 2014, which is a divisional of U.S. patent application Ser. No. 13/155,499 filed on Jun. 8, 2011, which claims the benefit of U.S. Provisional Application Ser. No. 61/352,560, filed on Jun. 8, 2010, the contents of which are herein incorporated by reference in their entirety.

FIELD OF THE INVENTION

The present invention relates to peristaltic pumps, and more particularly, to pump heads for peristaltic pumps.

BACKGROUND OF THE INVENTION

Peristaltic pumps generally involve the use of a moving pump head including a roller assembly with one or more rollers that completely or partially occludes a flexible conduit, or squeeze tube, to impel fluid therethrough. Peristaltic pumps are frequently employed in applications where it is critical that the fluid being pumped remain completely isolated; for instance, where highly reactive or radioactive fluids are being pumped, or in medical applications where stringent sterile conditions must be maintained. Additionally, since peristaltic pumps can function as positive displacement pumps (delivering a fixed volume of fluid at a given operating speed, regardless of system pressure), they are also useful in applications where a metered flow of fluid is required.

For various reasons, component wear in some peristaltic pumps can occur at an accelerated rate, requiring relatively frequent (compared to other pump types) repair or replacement of the pump head. With many conventional peristaltic pumps, pump head repair or replacement can be difficult and time-consuming.

SUMMARY OF THE INVENTION

In view of the foregoing, it is an object of the present invention to provide an improved peristaltic pump head and related methods. In particular, it is an object of the present invention to provide a peristaltic pump head that is more easily repaired or replaced. It is another object of the present invention to provide components for peristaltic pump heads that are more reliable and/or durable.

According to an embodiment of the present invention, a peristaltic pump head includes a housing assembly adapted for mounting to a drive mechanism, a roller assembly arranged with the housing assembly and a flexible conduit extending through the housing assembly and engageable by the roller assembly to impel fluid therethrough. The roller assembly and the flexible conduit are removable from the housing assembly without disconnecting the entire housing assembly from the drive mechanism.

According to an aspect of the present invention, the housing assembly includes a first housing section and a second housing section, the first housing section being releasably connected to the second housing section, and the second housing section being adapted for mounting to the drive motor.

According to another aspect of the present invention, the first housing section is configured for use as a tool to manually expand and contract the roller assembly.

According to another embodiment of the present invention, a roller assembly for a peristaltic pump head includes an axially extending drive shaft, a roller control body fixedly mounted to the drive shaft, at least a first end plate rotatably mounted about the drive shaft, and at least a first roller arm pivotably mounted to the first end plate. The first roller arm is expandable and collapsible by rotating the roller control body relative to the first end plate.

According to another embodiment of the present invention, a flexible conduit includes a length of hollow tubing made of an elastomeric material, and at least one overmolded end fitting made of a rigid polymeric material and fused to an end of the hollow tubing.

In a method aspect, the material of the end fitting has a higher melting point that the tubing blank such that the end of the tubing blank at least partially melts and fuses with the end fitting.

These and other objects, aspects and advantages of the present invention will be better appreciated in view of the drawings and following detailed description of preferred embodiments.

DETAILED DESCRIPTION OF PREFERRED EMBODIMENTS

Figure 1:
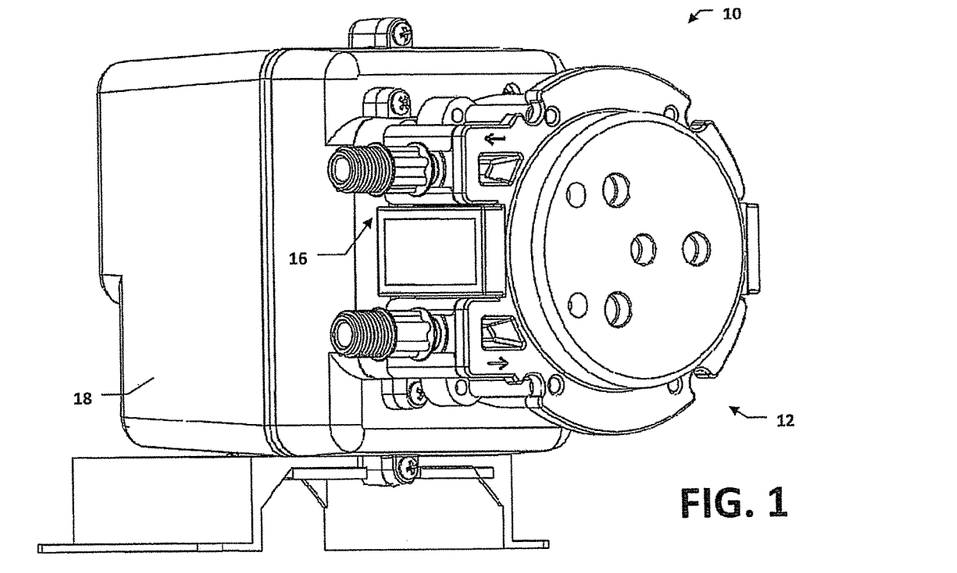
FIG. 1 is a perspective view of a peristaltic pump head, according to an embodiment of the present invention, mounted to a motor and including a housing assembly, a roller assembly and a flexible conduit.
Figure 2:
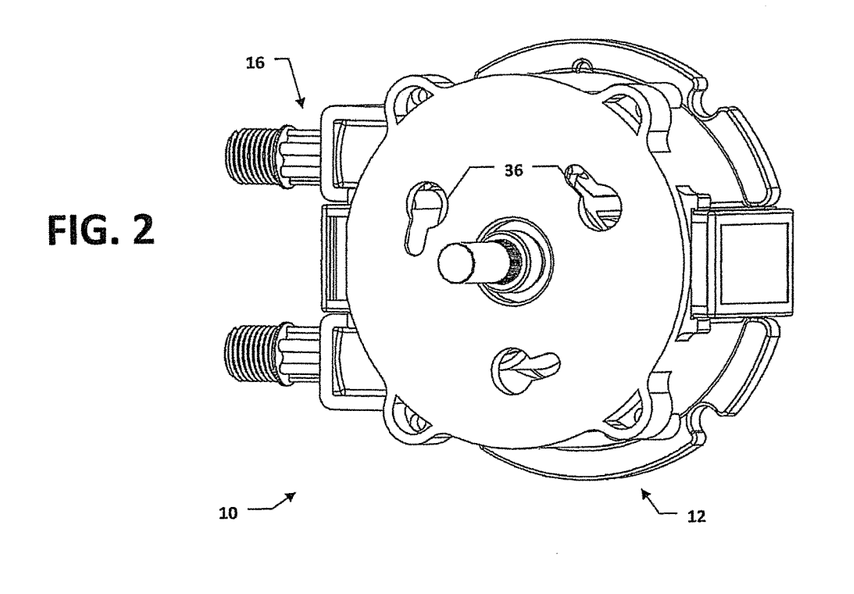
FIG. 2 is another perspective view of the pump head of FIG. 1.
Figure 3:
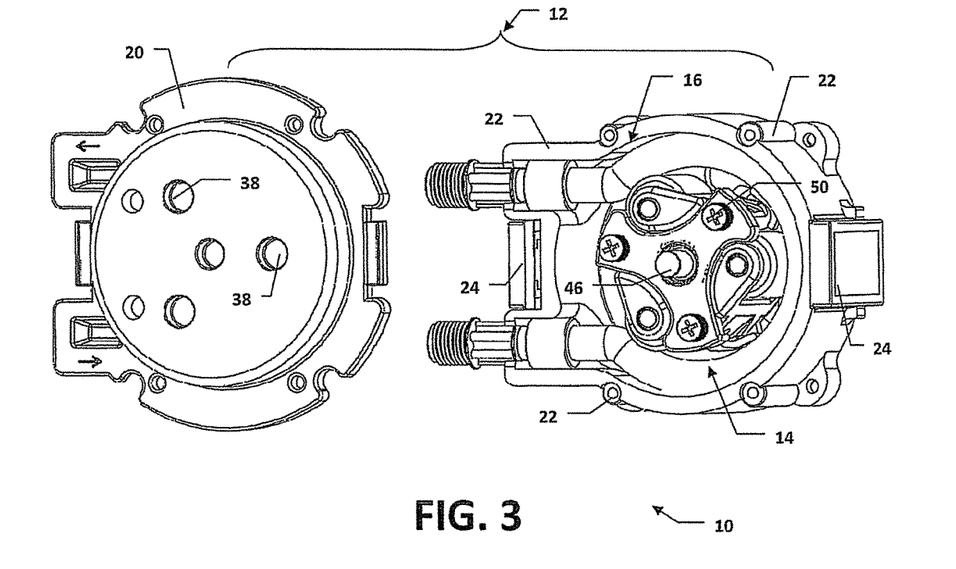
FIG. 3 is a partially exploded perspective view of the pump head of FIG. 1.

Referring to FIGS. 1-3, a peristaltic pump head 10 includes a housing assembly 12, a roller assembly 14 and a flexible conduit 16. The roller assembly 14 is rotatably mounted within the housing assembly 12 and is operable to selectively occlude portions of the flexible conduit 16 to forcibly move fluid therethrough. The peristaltic pump head 10 is mounted to a motor 18 or other drive mechanism.

Figure 4:
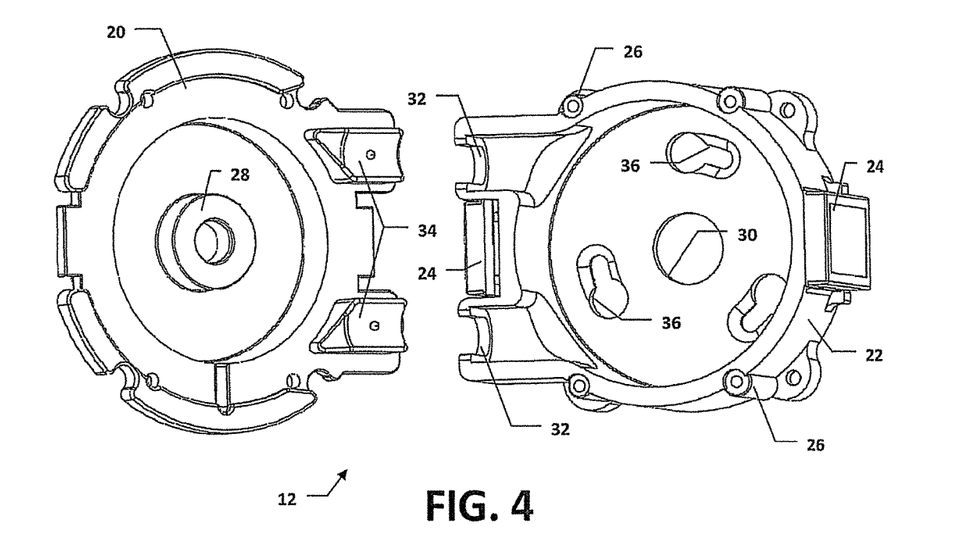
FIG. 4 is a partially exploded perspective view of the housing assembly of FIG. 1.

Referring to FIGS. 3 and 4, the housing assembly 12 includes a first housing section 20 and a second housing section 22 releasably connected by latches 24. Preferably, the housing assembly 12 is formed of a hard plastic material, such as a polycarbonate plastic, and at least the first housing section 20 is substantially transparent to afford a clear view of the roller assembly 14 and flexible conduit 16. To add additional strength, bosses 26 are formed in the second housing section 22. In lieu of, or in addition to the latches 24, the first and second housing sections 20, 22 can be connected by screws (not shown) threaded into the bosses 26 through overlying passages in the first housing section 20.

The first housing section 20 includes a roller assembly seat 28 and the second assembly housing 22 includes a substantially aligned roller assembly bore 30. Conduit slots 32 are formed in opposite edges of the second housing section 22, permitting the insertion of opposite ends of the flexible conduit 16 therein. The conduit slots 32 are generally opposed conduit protrusions 34 extending from the first housing section 20. The conduit slots 32 and protrusions 34 cooperate to secure the flexible conduit 16 ends therebetween.

Circumferentially extending keyhole mounting slots 36 are formed in a lower surface of the second housing section 22 to releasably secure the housing assembly 12 to a motor or other drive mechanism (not shown) for the roller assembly 14 of the pump head 10. Roller assembly engagement holes 38 are defined in an outer surface of the first housing section 20 to facilitate manual counter-rotation of the roller assembly 14, as will be explained in greater detail below.

Figures 5, 6:
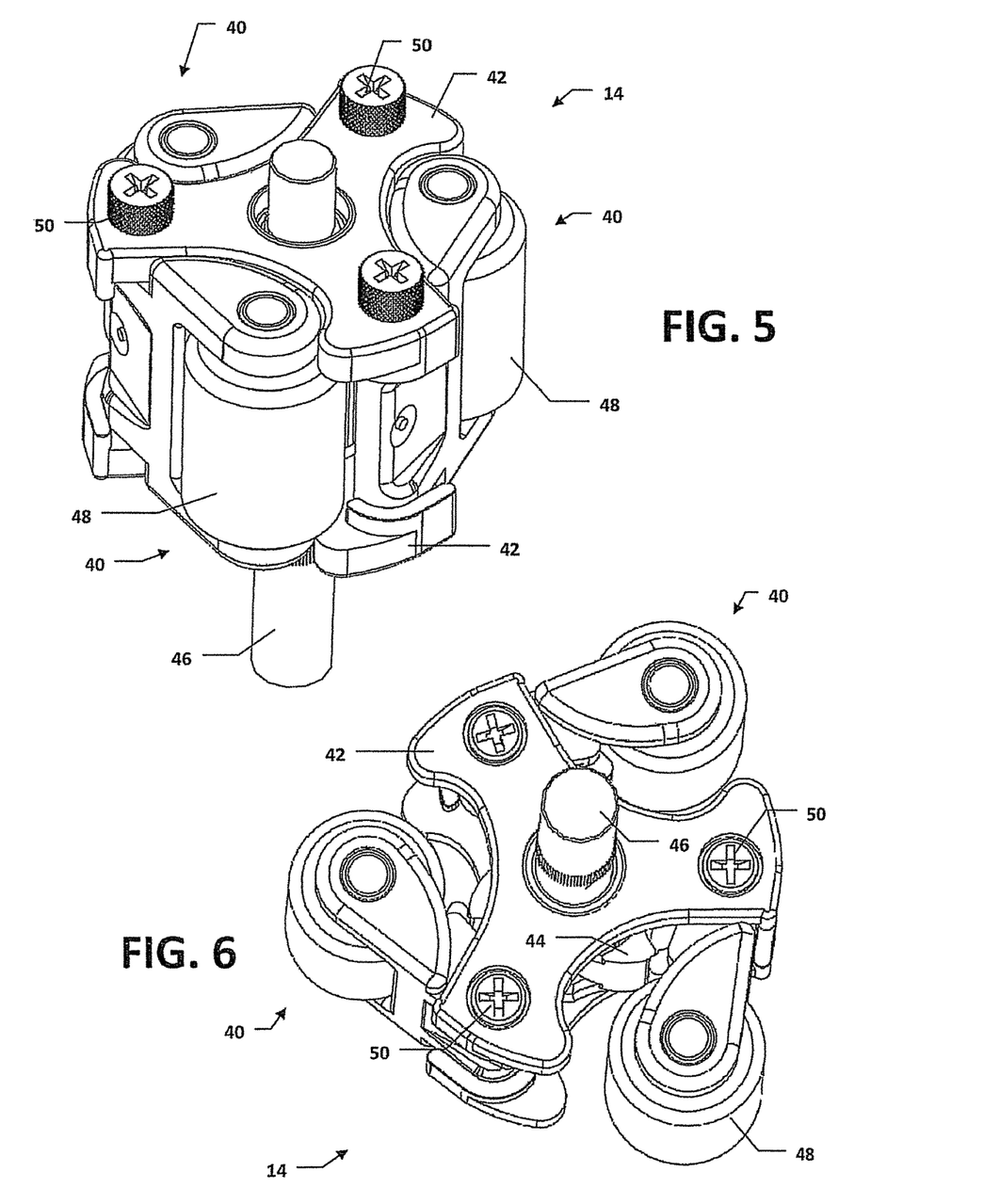
FIG. 5 is a perspective view of the roller assembly of FIG. 1, including roller arms, end plates and a roller control body.
FIG. 6 is a perspective view of the roller assembly of FIG. 4, in an alternate configuration.

Referring to FIGS. 5 and 6, the roller assembly 14 includes a plurality of roller arms 40, substantially opposed end plates 42, a roller control body 44, and an axially extending drive shaft 46. The roller arms 40, end plates 42 and control body 44 are preferably made from a high strength plastic or composite. Glass-filled polyphenylene sulfide (PPS) is particularly preferred for strength, rigidity and chemical resistance. The rollers 48 of the roller arms 40 are preferably formed with low friction surfaces to facilitate rotation.

The plurality of roller arms 40 are pivotally connected between the end plates 42 via mounting screws 50. On an end of the roller assembly 14 proximate to the first housing section 20, heads of screws 50 extend above the respective end plate 42 (as in FIG. 5). The end plates 42 are rotatably mounted to the drive shaft 46 around the roller control body 44 and are capable of limited rotational motion relative thereto. The roller control body 44 is fixedly mounted to the drive shaft 46.

Figure 7:
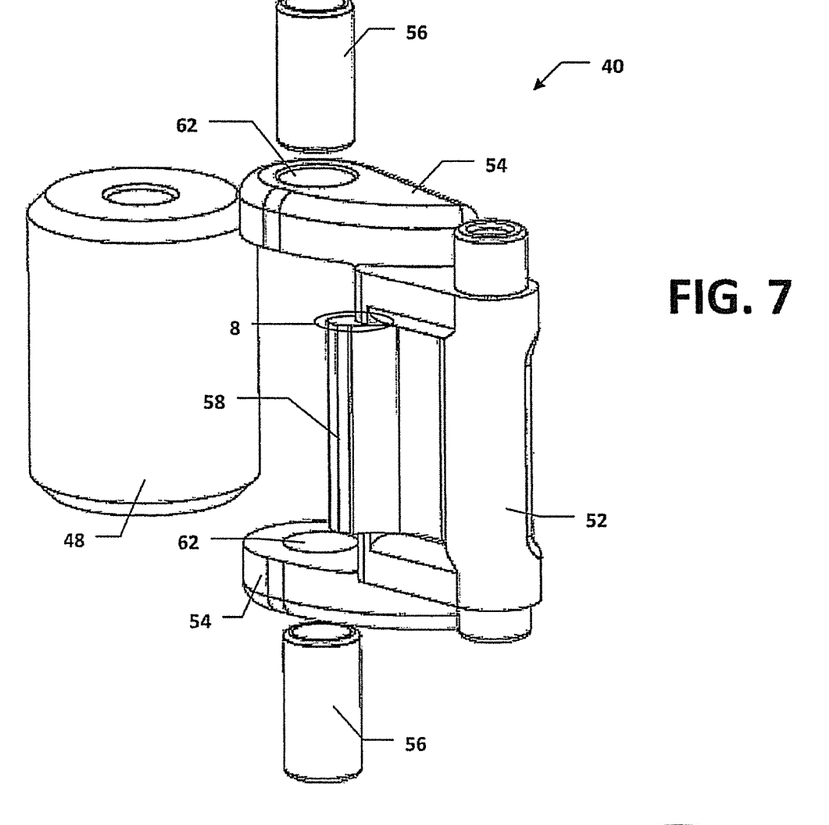
FIG. 7 is an exploded perspective view of one of the roller arms of FIG. 5.
Figure 8:
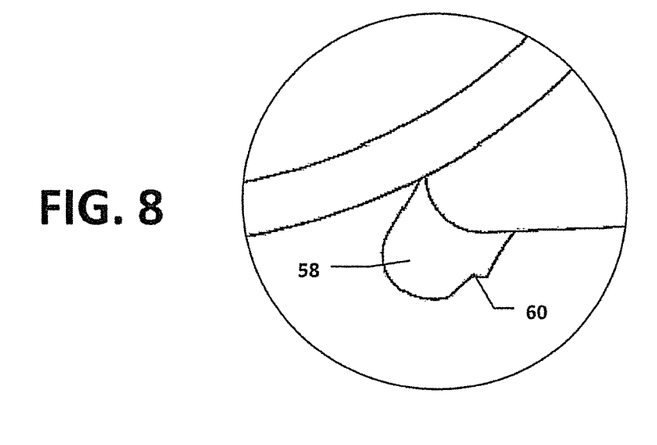
FIG. 8 is a detail top view of area 8 of FIG. 7.

Referring to FIG. 7, each roller arm 40 includes the roller 48, an end plate mounting body 52, roller mounting wings 54 and roller mounting pins 56. The end plate mounting body 52 and roller mounting wings 54 are preferably formed integrally as a single unit. The end plate mounting body 52 has bores therein to receive mounting screws 50 (see FIGS. 5 and 6). The mounting body 52 further includes a control body engagement protrusion 58 extending generally radially inwards therefrom. An axially extending locking detent 60 is defined near a distal edge the protrusions 58 (see FIG. 8).

The roller mounting wings 54 having roller mounting holes 62 defined therein for the receiving the roller mounting pins 56. Instead of separate pins 56, a single, longer pin or shaft could be used. The pins can be formed, for instance, from PPS, and support a bronze roller bushing, which in turn supports the roller 40.

Figure 9:
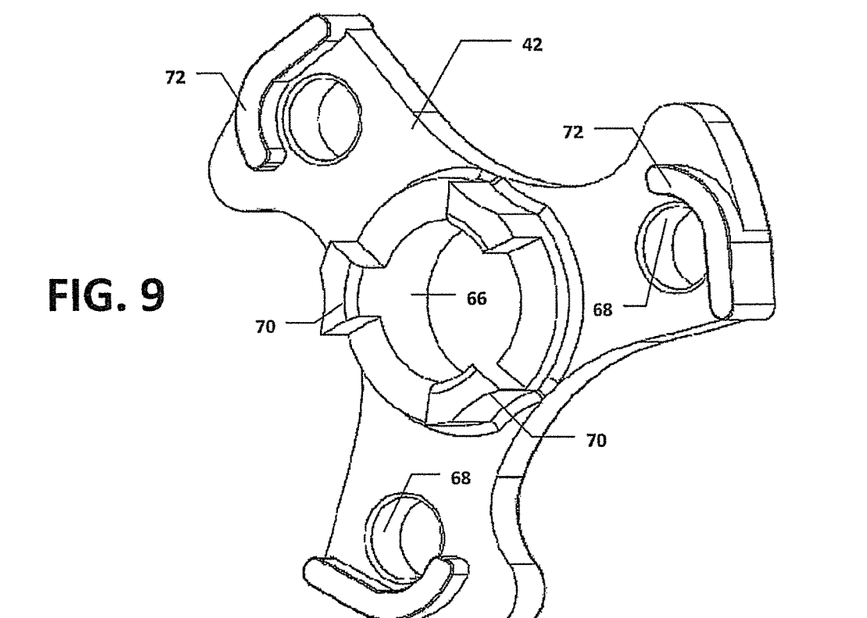
FIG. 9 is a perspective view of one of the end plates of FIG. 5.

Referring to FIG. 9, each end plate 42 defines a central end plate opening 66, for receiving the drive shaft 46 and roller control body 44 therethrough (see FIGS. 5 and 6), and roller arm openings 68 for receiving opposite ends of the mounting bodies 52 therein. Control body limiting lugs 70 protrude from around the central opening 66 and roller arm limiting ridges 72 protrude adjacent to the roller arm openings 68.

Figure 10:
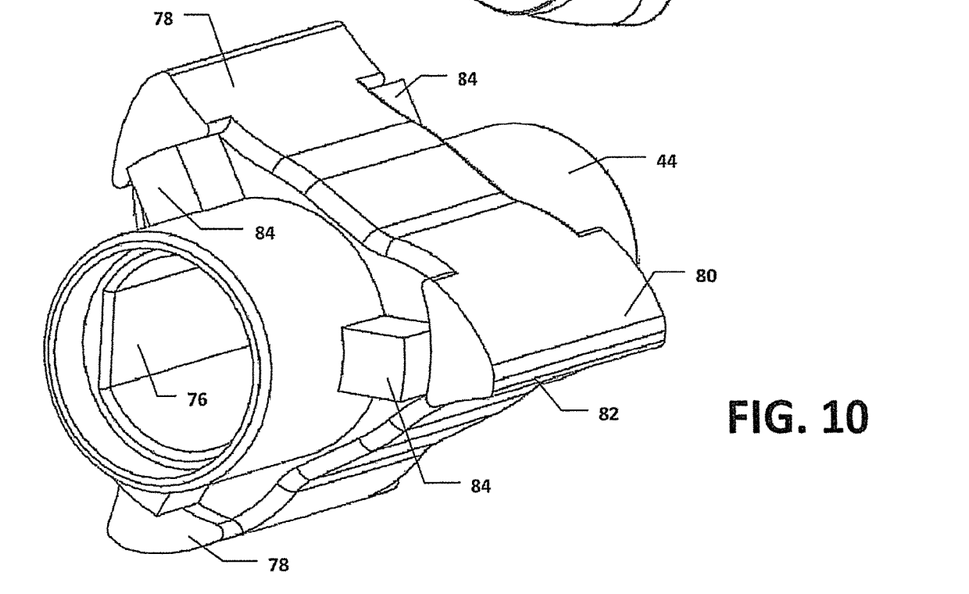
FIG. 10 is a perspective view of the roller control body of FIG. 5.

Referring to FIG. 10, the control body 44 defines a shaft opening 76 centrally therein. Expander cams 78 extend generally radially outward around the central opening 76. Each expander cam 78 includes a curved surface 80 terminating at an axially extending distal edge 82. Each distal edge 82 is dimensioned to closely engage a respective locking detent 60 (see FIG. 8). Control body stops 84 extend radially outwards from the shaft opening 76 adjacent each axial end of the expander cams 78.

Referring again to FIGS. 5 and 6, with the roller assembly 14 in the collapsed position (FIG. 5), rotation of the drive shaft 46 in a first direction (counter clockwise in FIG. 5, clockwise in FIG. 6) results in rotation of the control body 44 relative to the end plates 42 and roller arms 40. The expander cams 78 engage the rollers arms 40 and urge the arms 40 outwards into the expanded position (FIG. 6). Once in the expanded position, the distal edges 82 of the expander cams 78 are seated in the locking detents 60 of the control body engagement protrusions 58. This engagement inhibits inadvertent collapse of the roller assembly 14 due to external pressure exerted on the rollers 48.

To allow the roller assembly 14 to return to the collapsed position, the drive shaft 46 must be counter-rotated (clockwise in FIG. 5, counterclockwise in FIG. 6) to disengage the distal edges 82 of the expander cams 78 from the locking detents 60. Once the roller assembly 14 is fully expanded or collapsed, further rotation of the drive shaft 46 will rotate the entire roller assembly 14 as a unit. Preferably, approximately $\frac{1}{8}^{th}$ of a turn is sufficient to fully expand or collapse the roller assembly 14.

The control body limiting lugs 70 and roller arm limiting ridges 72 respectively inhibit over-rotation of the control body 44 (in either rotational direction) and excessive-pivoting of the roller arms 40, and facilitate rotation of the roller assembly 14 as a unit after expansion.

Figure 11:
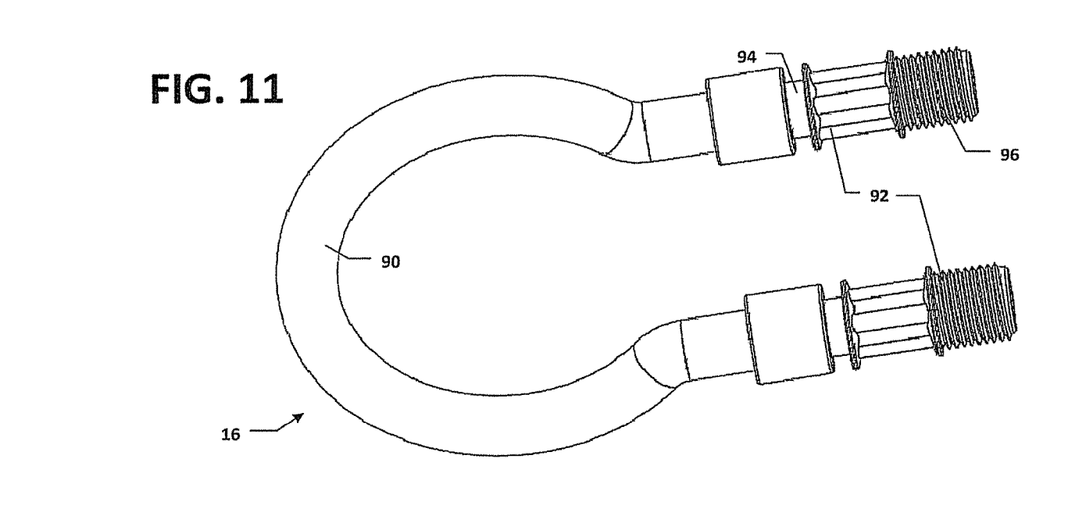
FIG. 11 is a perspective view of the flexible conduit of FIG. 1.
Figure 12:
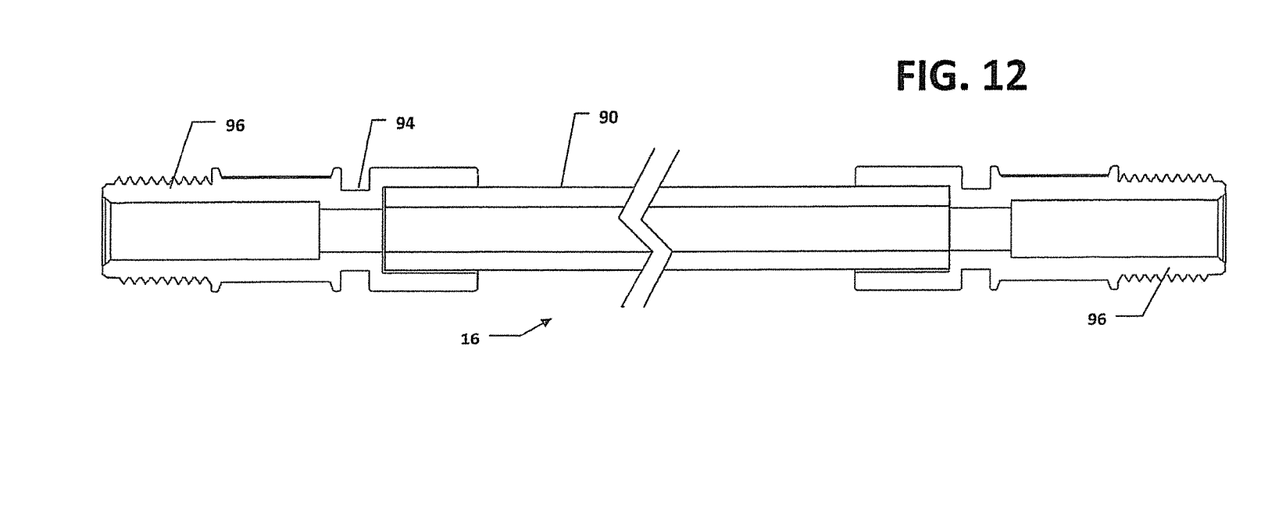
FIG. 12 is a sectional view of the flexible conduit of FIG. 1.

Referring FIGS. 11 and 12, the flexible conduit 16, also referred to as a squeeze tube, includes hollow tubing 90 extending between end fittings 92. The end fittings 92 include a reduced-diameter seating portion 94 for secure engagement within the conduit slots 32 (see FIG. 3), as well as threaded portions 96, or other suitable mating portions, for connection of the peristaltic pump head 10 within a larger fluid system. If desired, distal ends of the end fittings 92 can be chamfered. Additionally, the end fittings 92 can be textured, provided with protrusions or the like between the threaded portion 96 and the seating portions 94 to facilitate gripping when making or unmaking connections.

The hollow tubing 90 is preferably formed from an extruded, elastomeric tubing blank and the end fittings 92 are overmolded over opposite ends of the blank from a rigid polymeric material. Advantageously, the rigid polymeric material has a higher melting temperature than the tubing blank such that outer surfaces of opposite ends of the blank melt during the overmolding process and fuse with the end fittings 92, effectively forming an integral, one piece unit.

Where the flexible conduit 16 is to be formed as an integral, one piece unit, the hollow tubing 90 is preferably a thermoplastic elastomer, such as is sold under the trademark Santoprene™. The end fittings 92 are preferably a thermoplastic polymer, such as polypropylene or polyethylene, although other suitable materials can be selected with similar melting point relationships.

Additionally, in the depicted embodiment, only a portion of the end fittings 92 are overmolded over the tubing 90 ends. It will be appreciated that substantially the entire length of the end fittings 92 could be overmolded over the tubing 90 ends, such that fluid only comes into direct contact with the tubing 90 material. Also, an insert, preferably formed from the same material as the end fittings 92, can be inserted into the ends of the hollow tubing 90 prior to overmolding to prevent melted plastic from obstructing the interior of the tubing when the inner diameter of the tubing 90 is larger than the inner diameter of the overmolded end fitting 92.

Figure 13:
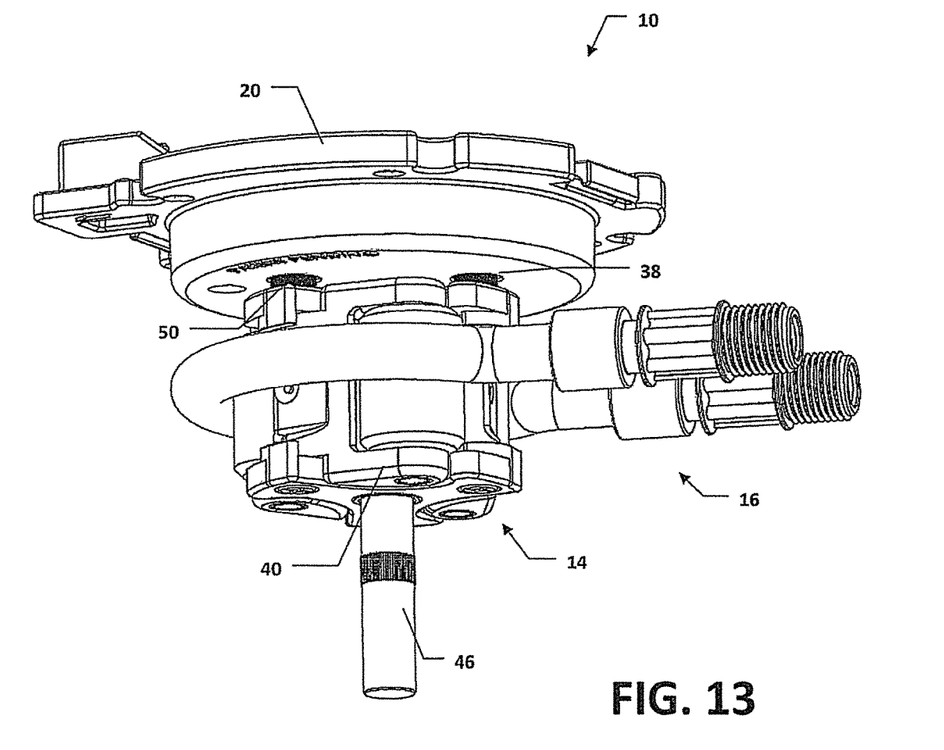
FIG. 13 a further perspective view of the pump head of FIG. 1, in an alternate configuration, with a portion of the housing assembly removed to show details.

Referring again to FIGS. 1-3, in use, the roller assembly 14 is installed onto the shaft 46 and the flexible conduit 16 is arranged thereabout, with opposite ends engaged in the conduit slots 32. The pump head 10 is secured to the motor 18 by the keyhole mounting slots 36 in the second housing section 22. Referring also to FIG. 13, the first housing section 20 is turned over and the roller assembly engagement holes 38 are placed over the outwardly extending heads of mounting screws 50 (the second housing section 22 is not shown to more clearly depict this engagement). To enhance engagement between the mounting screws 50 and the engagement holes 38, the heads of the screws 50 can be knurled or otherwise textured with a high friction surface.

The first housing section 20 is quickly rotated in the counterclockwise direction (with reference to FIG. 13) to expand the roller arms 40, as described above. The first housing section 20 is then removed from the heads of mounting screws 50, turned over and secured to the second housing section 22 with the latches 24. Connections are made between the end fittings 92 and the fluid system.

In the course of disassembling the pump head 10, it may be necessary to counter-rotate the roller assembly 14 to collapse the roller arms 40. To facilitate counter-rotation, the first housing section 20 is unlatched, removed and turned over. The roller assembly engagement holes 38 are placed over the extending heads of mounting screws 50. The first housing section 20 is then used as a tool to facilitate counter-rotation.

It will be appreciated from the foregoing that replacement of the roller assembly 14 and/or flexible conduit 16 is easily performed by disengaging the latches 24 and removing the first housing section 20. Dismounting or replacement of the entire pump head 10 is not required. Additionally, the first housing section 20 can, itself, be used to facilitate expansion and collapse of the roller assembly 14, eliminating the need for extra tools.

The above embodiments are provided for exemplary and illustrative purposes; the present invention is not necessarily limited thereto. For instance, various aspects and features of the depicted embodiment could readily be integrated with other pump head components. As another example, other latching and mating features for the housings could readily be employed. Additionally, the present invention is not necessarily limited to pump heads with three rollers, and other suitable numbers and configurations of rollers could be used. Also, the present invention is not necessarily limited to a particular amount of curvature traversed by the roller assembly. For example, aspects of the present invention can be applied in connection 360 degree pump heads, as well as linear peristaltic pumps. Also, unless otherwise indicated, directional terms are used for ease of reference and do not limit the invention to a particular orientation.

Those of ordinary skill in the art will appreciate that these and other combinations and modifications, as well as adaptations to particular circumstances, will fall within the scope of the invention as herein shown and described and of the claims appended hereto.

What is claimed is:

1. A peristaltic pump head comprising:
   a housing assembly adapted for mounting to a drive mechanism;
   a roller assembly arranged with the housing assembly; and
   a flexible conduit extending through the housing assembly and engageable by the roller assembly to impel fluid therethough;
   wherein the roller assembly and the flexible conduit are removable from the housing assembly without disconnecting the entire housing assembly from the drive mechanism;
   wherein the housing assembly includes:
      a first housing section;
      a second housing section adapted for mounting to the drive mechanism; and
      at least one connector for releasably connecting the first housing section to the second housing section;
   wherein the roller assembly includes at least one expandable and collapsible roller arm;
   wherein the first housing section is configured for use as a tool to manually rotate the roller assembly; and
   wherein an end of the roller assembly proximate to the first housing section includes at least one extension and the first housing section defines at least one roller assembly engagement hole defined in an outer surface thereof, such that the first housing section, when removed from the second housing section, is turned over and the at least one extension is engaged by the at least one roller assembly engagement hole to manually rotate the roller assembly.

2. The pump head of claim 1, wherein the at least connector include at least one latch.

3. The pump head of claim 1, wherein the first housing section defines a roller assembly seat for seating an upper end of a drive shaft of the roller assembly.

4. The pump head of claim 3, wherein the second housing section defines a roller assembly bore substantially aligned with the roller assembly seat.

5. The pump head of claim 1, wherein the housing assembly includes a pair of conduit slots where ends of the flexible conduit exit the housing assembly.

6. The pump head of claim 5, wherein the housing assembly further includes a pair of conduit protrusions generally opposed to the conduit slots and cooperating therewith to secure the flexible conduit ends therebetween.

7. The pump head of claim 6, wherein the conduit slots are arranged on one of the first housing section or the second housing section and the conduit protrusions are arranged on the other of the first housing section or the second housing section.

8. The pump head of claim 7, wherein the conduit slots are arranged on the second housing section.

9. The pump head of claim 5, wherein the flexible conduit ends include end fittings having reduced diameter seating portions engaged in the conduit slots.

10. The pump head of claim 1, wherein the roller assembly is configured such that rotation in a first direction expands the roller arm and rotation in a second direction collapses the roller arm.

11. The pump head of claim 1, wherein the at least one extension is a head of screw securing the at least one roller arm to an end plate of the roller assembly.

12. The pump head of claim 1, wherein there are a plurality of extensions on the end of the roller assembly proximate to the first housing section and the first housing section defines a plurality roller assembly engagement holes configured to simultaneously engage the plurality of extensions to manually rotate the roller assembly.

* * * * *